US008611626B2

(12) United States Patent
Miao et al.

(10) Patent No.: US 8,611,626 B2
(45) Date of Patent: Dec. 17, 2013

(54) SYSTEM AND METHODS FOR FAST IMPLEMENTATION OF EQUALLY-SLOPED TOMOGRAPHY

(75) Inventors: Jianwei Miao, Los Angeles, CA (US);
Yu Mao, Los Angeles, CA (US);
Benjamin Pooya Fahimian, Beverly Hills, CA (US)

(73) Assignee: The Regents of the University of California, Oakland, CA (US)

( * ) Notice: Subject to any disclaimer, the term of this patent is extended or adjusted under 35 U.S.C. 154(b) by 725 days.

(21) Appl. No.: 12/771,449

(22) Filed: Apr. 30, 2010

(65) Prior Publication Data
US 2010/0284596 A1    Nov. 11, 2010

Related U.S. Application Data

(60) Provisional application No. 61/174,303, filed on Apr. 30, 2009.

(51) Int. Cl.
*G06K 9/00* (2006.01)
*G06K 9/36* (2006.01)

(52) U.S. Cl.
USPC .......................................... 382/131; 382/280

(58) Field of Classification Search
USPC .................................. 382/280, 131
See application file for complete search history.

(56) References Cited

U.S. PATENT DOCUMENTS

| 4,506,327 | A |  | 3/1985 | Tam |  |
|---|---|---|---|---|---|
| 4,616,318 | A |  | 10/1986 | Crawford |  |
| 4,752,879 | A |  | 6/1988 | Brunnett |  |
| 4,888,693 | A |  | 12/1989 | Tam |  |
| 5,751,243 | A | * | 5/1998 | Turpin | 342/179 |
| 5,761,267 | A |  | 6/1998 | Besson |  |
| 5,937,102 | A |  | 8/1999 | Jin |  |
| 6,304,317 | B1 |  | 10/2001 | Taniguchi et al. |  |
| 6,366,638 | B1 |  | 4/2002 | Hsieh |  |
| 6,687,418 | B1 | * | 2/2004 | Ludwig | 382/280 |

(Continued)

FOREIGN PATENT DOCUMENTS

| WO | 2007026234 A1 | 3/2007 |
|---|---|---|
| WO | 2008017076 A2 | 2/2008 |

OTHER PUBLICATIONS

Incomplete-Data CT Image Reconstructions in Industrial Applications, K.C. Tam, J.W. Eberhard, K.W. Mitchell, IEEE Transactions on Nuclear Science, vol. 37, No. 3, Jun. 1990.*

(Continued)

*Primary Examiner* — Michelle Entezari
(74) *Attorney, Agent, or Firm* — John P. O'Banion (57) ABSTRACT

A system and method for projection number and radiation dose reduction in tomographic imaging that creates a three dimensional cross sectional image of an object by the reconstruction of its projections. Images of a superior quality can be obtained with a fewer number projections than seen with conventional methods by reconstruction of projections that have been pre-processed and preferably placed in the Fourier domain with a Fractional Fourier Transform (FrFT) or forward Pseudo-polar Fast Fourier transform (PPFFT). The projections are iteratively refined through formulation of a constrained optimization problem with constraints in object space and Fourier space preferably solved with a gradient descent algorithm incorporating a Bregman iterative regularization or a continuative regularization. By using an exact Fourier-based iterative algorithm as well as physical and mathematical constraints, convergence to a lowest-possible noise state that is also strictly consistent with the measured data can be obtained.

18 Claims, 4 Drawing Sheets

(56) References Cited

U.S. PATENT DOCUMENTS

| | | | |
|---|---|---|---|
| 6,744,848 B2 | 6/2004 | Stanton | |
| 6,862,337 B2 | 3/2005 | Claus et al. | |
| 6,873,744 B2 | 3/2005 | Ottesen | |
| 6,920,240 B2 | 7/2005 | Rodet et al. | |
| 7,054,504 B2* | 5/2006 | Ludwig | 382/280 |
| 7,076,091 B2 | 7/2006 | Rosenfeld | |
| 7,209,535 B2 | 4/2007 | Chen et al. | |
| 7,315,636 B2 | 1/2008 | Kuduvalli | |
| 7,436,507 B2 | 10/2008 | Moribe | |
| 7,439,739 B2 | 10/2008 | Beatty | |
| 7,627,195 B2* | 12/2009 | Ludwig | 382/280 |
| 7,697,777 B2* | 4/2010 | Ludwig | 382/255 |
| RE42,187 E * | 3/2011 | Ludwig | 382/280 |
| 8,094,961 B2* | 1/2012 | Ludwig | 382/255 |
| 8,094,969 B2* | 1/2012 | Ludwig | 382/280 |
| 8,270,760 B2* | 9/2012 | Miao et al. | 382/280 |
| 8,442,341 B2* | 5/2013 | Ludwig | 382/255 |
| 8,442,342 B2* | 5/2013 | Ludwig | 382/255 |
| 2003/0095596 A1 | 5/2003 | Shimizu | |
| 2003/0198403 A1 | 10/2003 | Ottesen | |
| 2004/0076257 A1 | 4/2004 | McDaniel | |
| 2004/0215072 A1 | 10/2004 | Zhu | |
| 2004/0264634 A1* | 12/2004 | Claus et al. | 378/21 |
| 2005/0047636 A1* | 3/2005 | Gines et al. | 382/131 |
| 2007/0003122 A1 | 1/2007 | Sirohey et al. | |
| 2007/0053477 A1 | 3/2007 | Ning | |
| 2007/0160304 A1 | 7/2007 | Berkner | |
| 2007/0232890 A1 | 10/2007 | Hirota | |
| 2008/0273651 A1* | 11/2008 | Boas | 378/4 |
| 2009/0221920 A1* | 9/2009 | Boppart et al. | 600/476 |
| 2009/0232377 A1 | 9/2009 | Miao et al. | |
| 2009/0262118 A1* | 10/2009 | Arikan et al. | 345/473 |
| 2011/0007980 A1 | 1/2011 | Fahimian et al. | |
| 2011/0044546 A1* | 2/2011 | Pan et al. | 382/195 |
| 2011/0164799 A1 | 7/2011 | Miao et al. | |

OTHER PUBLICATIONS

Miao, Jianwei, Friedrich Förster, and Ofer Levi. "Equally sloped tomography with oversampling reconstruction." Physical Review B 72, No. 5 (2005).*

Ozaktas, Haldun M., Orhan Arikan, M. Alper Kutay, and Gozde Bozdagt. "Digital computation of the fractional Fourier transform" Signal Processing, IEEE Transactions on 44, No. 9 (1996): 2141-2150.*

Yin, Wotao, Stanley Osher, Donald Goldfarb, and Jerome Darbon. "Bregman iterative algorithms for l1 -minimization with applications to compressed sensing." SIAM Journal on Imaging Sciences 1, No. 1 (2008): 143-168.*

Mao, Yu et al.—"Development and Optimization of Regularized Tomographic Reconstruction Algorithms Using Equally-Sloped Tomography"—IEEE Transactions on Image Processing, vol. 19, No. 5, May 2010, pp. 1259-1268.

Korean Intellectual Property Office (KIPO), International Search Report and Written Opinion dated Sep. 1, 2009, including claims searched, related PCT Application No. PCT/US2009/032733, pp. 1-10.

Korean Intellectual Property Office (KIPO), International Search Report and Written Opinion dated Feb. 18, 2010, including claims searched, related PCT Application No. PCT/US2009/051290, pp. 1-11.

State Intellectual Property Office of P.R. China, the Notification of the First Office Action (translation) issued on Jun. 9, 2010, related Chinese Patent Application No. 200780028681.0, counterpart to PCT/US20081075220, with claims examined, pp. 1-18.

Miao, J. et al.—"Three-Dimensional GaN-Ga2O3 Core Shell Structure Revealed by X-Ray Diffraction Microscopy"—Phys. Rev. Lett. 97, 2006, pp. 215503-1-215503-4.

Averbuch, a. et al.—"Fast and Accurate Polar Fourier Transform"—App. Comput. Harmon. Anal. 21, 2006, pp. 145-167.

United States Patent and Trademark Office (USPTO), International Search Report and Written Opinion dated Apr. 10, 2008, including claims searched, related PCT Application No. PCT/US2007/075220, pp. 1-21.

State Intellectual Property Office of P.R. China, the Notification of the Second Office Action (translation) issued Jun. 15, 2011, related Chinese Patent Application No. 200780028681.0, counterpart to PCT/US2008/075220, with claims examined, pp. 1-16.

Korean Intellectual Property Office (KIPO), International Search Report and Written Opinion dated Dec. 16, 2010, including claims searched, related PCT Application No. PCT/US2012/033162, pp. 1-12.

European Patent Office, Extended European Search Report issued on Oct. 31, 2011, related EPO Patent Application No. 07840699.8, counterpart to PCT/US2007/075220, with claims searched, pp. 1-14.

Delaney, A.H. et al.—"A Fast and Accurate Fourier Algorithm for Iterative Parallel-Beam Tomography"—IEEE Trans. on Image Processing, vol. 5, No. 5, May 1996, pp. 740-753.

Ye, J. et al.—"A Self-Referencing Level-Set Method for Image Reconstruction from Sparse Fourier Samples"—Int. Jour. of Computer Vision, vol. 50, No. 3, 2002, pp. 253-270.

Erlandsson, K. et al.—"A New 3D Backprojection and Filtering Method for Pet Using All Detected Events"—IEEE Trans. on Nuclear Science, vol. 45, No. 3, Jun. 1998, pp. 1183-1188.

Olson, T.—"Limited Angle Tomography Via Multiresolution Analysis and Oversampling"—Proc. of the IEEE Time-Frequency and Time-Scale Analysis, Oct. 4, 1992, pp. 215-218.

Australian Government, IP Australia, Examiner's First Report dated Nov. 30, 2011, related AU Application No. 2007281076, counterpart to PCT/US2007/075220, with claims examined, pp. 1-23.

European Patent Office, European Supplementary Search Report issued on Mar. 1, 2013 (pp. 1-5) for corresponding European Patent Application No. 10770419.9 (International Patent Application No. PCT/US2010033162) with claims searched (pp. 6-8) pp. 1-8.

Yu Mao, et al., "Development and Optimization of Regularized Tomographic Reconstruction Algorithms Utilizing Equally-Sloped Tomography," Mar. 15, 2003, pp. 1-10, Retrieved from the internet: //ftp.math.ucla.edu/publ/camreporticam09-27.pdf on Feb. 20, 2013.

Lee et al., "Rediation dose reduction and image enhancement in biological imaging through equally-sloped tomography," Journal of Structural Biology, Academic Press, US, vol. 164, No. 2, Nov. 1, 2008, pp. 221-227.

* cited by examiner

FIG. 5

SYSTEM AND METHODS FOR FAST IMPLEMENTATION OF EQUALLY-SLOPED TOMOGRAPHY

CROSS-REFERENCE TO RELATED APPLICATIONS

This application claims priority from U.S. provisional patent application No. 61/174,303 filed on Apr. 30, 2009, incorporated herein by reference in its entirety.

This application is related to U.S. patent application Ser. No. 12/363,079 filed on Jan. 30, 2009 and published as U.S. Patent Application Publication No. US 2009-0232377 A1 on Sep. 17, 2009, incorporated herein by reference in its entirety.

This application is related to PCT international patent application number PCT/US2007/075220 filed on Aug. 3, 2007 and published as WO 2008/017076 on Feb. 7, 2008, incorporated herein by reference in its entirety.

This application is related to U.S. provisional patent application No. 60/835,552 filed on Aug. 3, 2006, incorporated herein by reference in its entirety.

This application is related to PCT international patent application number PCT/US2009/032733 filed on Jan. 30, 2009 and published as WO 2009/097580 on Aug. 6, 2009, incorporated herein by reference in its entirety.

This application is related to U.S. provisional patent application No. 61/024,762 filed on Jan. 30, 2008, incorporated herein by reference in its entirety.

This application is related to PCT international patent application number PCT/US2009/051290 filed on Jul. 21, 2009 and published as WO 2010/011676 on Jan. 28, 2010, incorporated herein by reference in its entirety.

This application is related to U.S. provisional patent application No. 61/083,105 filed on Jul. 23, 2008, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to diagnostic and interventional imaging systems that use beams and detectors such as tomography, and more particularly to systems and methods for creating three dimensional cross sectional images of an object by the reconstruction of its projections that have been iteratively refined through modification in object space and Fourier space that permits object dose reduction and image enhancement.

2. Description of Related Art

Tomography has had a revolutionary impact in a number of fields, particularly biology and medicine. While the experimental implementation of tomography differs across different modalities, the central problems associated with its mathematical implementation are similar. On the one hand, an accurate image reconstruction is desired, requiring a high number of projections with minimal noise. On the other hand, the radiation dose imparted to biological specimens or a patient in computed tomography (CT) is a major concern. A primary challenge of tomography systems is the faithful reconstruction of an image with minimal noise from a limited number of noisy projection measurements.

Conventional tomography is an imaging technique that produces a cross-sectional 2D or 3D image of the internal structures of an object through analysis of planar projections. The typical tomography apparatus contains a radiation source and a detector that is rotated around an axis extending perpendicularly from the plane of the examination table. Projections of the patient or object are normally taken at equal angle intervals such that the angle of the radiating source with respect to the isocenter of the scanner changes by a fixed amount from one projection to the next. Images have been produced from several different beam sources including x-rays, electrons, gamma rays, ions, neutrons, sound waves and others.

One significant problem encountered with traditional tomographic imaging systems is the degradation of resolution and other image quality parameters due to the occurrence of missing or incomplete sets of projection data. Missing projection data can arise from radiation dose restrictions or from practical mechanical limitations in the imaging procedure or imaging system. One example is the missing wedge problem that occurs in electron microscopy, i.e., specimens cannot be tilted beyond ±70° and the data in the remaining ±20° projections are missing. These difficulties currently limit the resolution of the 3D imaging of cellular and organelle structures.

Since the radiation dose is proportional to the number of projections that are taken, and since tomographic imaging naturally requires a high number of projections for a suitable reconstruction, common tomographic devices can impart a significant radiation dose to patients as a result of the imaging procedure. With the increasing popularity of medical x-ray CT and fluoroscopic interventional imaging procedures, the long term effects of exposing patients to such ionizing radiation is of increasing clinical concern, especially for pediatric patients.

In addition to the problems of radiation dose and missing projection data, conventional image reconstruction algorithms suffer from inaccuracies arising from interpolation limitations. Since conventional tomography reconstructs a 3D object from a set of equally angled 2D projections, the manner of acquisition inherently forces the projection data into a polar format. Because the set of acquired projections are in polar coordinates and the object is in Cartesian coordinates, interpolation must be used in the reconstruction process either in object space or in Fourier space. Such interpolations may account for a large source of error from the reconstruction algorithm alone and result in a significant degradation of image quality as measured by the resolution, contrast, and signal to noise ratio.

Currently, the most widely used slice reconstruction algorithm is the filtered back projection (FBP). The filtered back projection scheme is computationally fast, but does not offer any solutions for the problem of excessive radiation dose exposure and the problem of image degradation due to missing projection data. In addition, FBP suffers from inaccuracies due to inherent interpolation problems that occur in the back projection process. As a result of the problem of missing projection data and the problem of interpolation, images reconstructed with the FBP method often contain artifacts that degrade the resolution and overall image quality.

For example, conventional FBP reconstruction algorithms merely give one solution from the entire solution set. Such reconstructions are well known to contain grainy, unphysical noise which degrades the image quality and limits the visibility of low contrast objects. Furthermore, since the noise in the projections and resulting image is correlated to the particle fluence at the detectors, high particle fluences are required for conventional methods in order to manage the noise in the reconstructed image resulting in high radiation doses to patients.

In addition to FBP, other reconstruction algorithms exists that are not in general use because they are computationally expensive under practical imaging conditions and also suffer from the problem of interpolation, which reveals itself when the forward projection process is modeled into the system matrix. These methods are also very sensitive to experimental noise and often diverge under realistic noisy experimental situations if the noise is not correctly modeled into the algorithm.

It can be seen that reconstruction algorithms currently existing in the art such as Filtered Back Projection are not mathematically exact and consequently may produce images of lower resolution, contrast, and signal to noise ratio than what may be possible. These limitations introduce inherent errors in the reconstructed image that result primarily from the reconstruction algorithm itself as opposed to experimental error.

Some reconstruction algorithms, such as the Estimated Maximum algorithms and maximum a posteriori algorithms have been specifically developed to arrive at a less noisy solution through a maximization or minimization of some objective parameter relating to the image noise. However, such algorithms have not been incorporated into the clinic and are limited in their application and accuracy because 1) the noise must be physically modeled before hand, which in most cases may be difficult or impossible; 2) If accurate physical models are not used, the algorithms diverge resulting in worse reconstructions than produced by conventional imagers; and 3) The current algorithms are not capable of including physical constraints, which may change from one patient to another.

Furthermore, due to the degradation of image quality, conventional methods of tomography require a high dose of radiation to be administered to a patient to produce suitable images. Consequently, conventional methods have a significantly higher probability of inducing secondary effects such as radiation damage or carcinogenesis to the patient.

Accordingly, there is a need for a system and method for tomographic imaging that limits the exposure of the subject to potentially harmful or destructive radiation that is at the same time accurate, reliable and computationally practical. There is also a great need for devices and methods with higher resolution and image quality. The present methods satisfy these needs, as well as others, and are generally an improvement over the art.

BRIEF SUMMARY OF THE INVENTION

The system and methods of the present invention are adaptable to any imaging technique that utilizes tomography to mathematically reconstruct the cross section of an object from its projections. The methods also allow a significant reduction of radiation dose imparted to the imaging object with a substantial improvement of image quality over conventional reconstruction techniques. The invention can be applied to variety of fields including physics, biology, material science, medicine, archeology, etc. The methods can also be implemented on current tomographic imaging systems such as CT or CAT scanners using photons (such as medical kilovoltage or megavoltage x-ray CT scanners, or small animal scanners such as x-ray MicroCT), Positron Emission Tomography (PET), Single Photon Emission Tomography (SPECT), parallel beam transmission CT (such as electron tomography, phase contrast x-ray CT), 3D Ultrasound, and any other tomographic imaging systems.

The present invention uses new tomographic reconstruction methods that allow for the fast and optimized implementation of Equally-Sloped Tomography' (EST), which eliminates the interpolative inaccuracies that are observed in conventional reconstruction methods. The invention also allows for dose reduction and image enhancement relative to conventional methods.

One deficiency present in some EST applications in time sensitive computed tomography (CT) modalities, such as the various medical x-ray CT modalities, lies in its comparatively slower speed due to its higher computation requirements. While the EST iterative algorithm makes superior image reconstructions, one limitation is the speed of the inverse pseudo-polar Fourier transform (PPFFT), which is more than one order slower than the forward PPFFT, and therefore hinders its broad application. The present invention provides two iterative algorithms that eliminate the use of the inverse PPFFT in conventional EST.

Improved computation speed in an EST image reconstruction is formulated as a constrained problem and subsequently transforming it into a series of linear problems which can be accurately solved by the operator splitting method or other similar method. Based on these mathematical developments, two iterative algorithms incorporating Bregman iterative regularization or continuative regularization are used. As described in greater detail elsewhere, the invention may also include additional procedures (such as pre-processing), incorporation of physical and mathematical constraints, (post-processing) and methodologies for the purpose of dose reduction and/or image enhancement described in the implementation of image reconstruction.

An aspect of the invention is to provide a system and method that can provide detailed two and three dimensional images from a reduced number of projections as well as reduced radiation flux over existing methods to reduce the exposure of the subject to radiation.

Given any tomographic modality, tomographic projections are acquired and pre-processed. Such pre-processing procedures may include: binning, smoothing, denoising, scatter correction, uniformity corrections, mathematical transformation (such as changing the detected intensities to more desired functionals for reconstruction, i.e. changing intensities to attenuation coefficients), of the projection data among others.

If the modality does not utilize parallel beam geometry, such as medical megavoltage and kilovoltage x-ray CT scanners that utilize divergent fan/cone beam geometries, any rebinning transformation found in the art may be utilized to transform the data into parallel beam format at angles determined by the user. Algorithms are then used to change the divergent or other beam geometries into parallel beam format so that such projection data can be incorporated into the reconstruction methods of the invention.

In the preferred embodiment of the invention, these angles correspond to the angles of the user determined lines of the 'equally-sloped' pseudopolar grid. Alternatively, these angles can be any general format and the present invention includes any methodology that interpolates the data from these angles to the lines of the pseudopolar grid in Fourier space.

After this preprocessing, a set of parallel beam projections are preferably obtained and transformed into the Fourier domain, preferably using the Fractional Fourier Transform (FrFT) to produce the experimental Fourier slices.

Preferably, the method includes formulating an equally sloped tomography image reconstruction as a constrained problem. The constrained problem is then transformed into a series of linear problems. The series of linear problems are then solved by the operator splitting method. Bregman iterative regularization or continuative regularization may then be applied.

Generally, the pre-processed slices are iteratively cycled back and forth between Fourier and object domains. Physical and mathematical constraints can be applied in the object domain, while the calculated slices are replaced with the corresponding measured ones in the Fourier domain, resulting in a compromise between the enforced constraints and the measured data. The algorithm converges to a solution which satisfies all the constraints as much as possible.

Compared to the traditional FBP, the methods do not require any direct interpolations, and reconstruct an image by searching for the most regularized image that is consistent with the experimental measurements. The EST Bregman and the EST continuation embodiments not only improve the image quality, but also significantly reduce the computational time. Most importantly, the methods can reduce the radiation dose by 80%-90%, while producing an image that is comparable to an image by FBP at a full dose.

The reasons that EST allows for significant reduction of the CT dose are because (i) an exact Fourier-based iterative algorithm is used in the reconstruction where both physical and mathematical constraints can be naturally incorporated, (ii) the algorithm is guided towards a lowest-possible noisy state, which is also strictly consistent with the measured data.

According to another aspect of the invention, a method of processing an image is provided, comprising: acquiring a tomographic projection, pre-processing the tomographic projection, applying a rebinning transformation to transform the data into parallel beam format at predetermined angles, transforming generated parallel beam projections into the Fourier domain using Fractional Fourier Transform (FrFT), and applying Pseudo-Polar Fast Fourier Transform to transform between object space on a Cartesian grid and the frequency domain on a pseudo-polar grid.

In one embodiment, the pre-processing comprises one or more of the following: binning, smoothing, denoising, scatter correction, uniformity corrections, mathematical transformation or the projection data.

In another embodiment, pre-processing comprises changing detected intensities to attenuation coefficients.

In yet another embodiment, the predetermined angles correspond to the angles of user determined lines of the 'equally-sloped' pseudopolar grid. Data from the predetermined angles is used to interpolate to lines of the pseudopolar grid in Fourier space.

Another aspect is providing a system for processing a tomographic image comprising the steps of acquiring a tomographic projection, pre-processing the tomographic projection, applying a rebinning transformation to transform the data into parallel beam format at predetermined angles, transforming generated parallel beam projections into the Fourier domain using Fractional Fourier Transform (FrFT), and applying Pseudo-Polar Fast Fourier Transform to transform between object space on a Cartesian grid and the frequency domain on a pseudo-polar grid.

Another aspect of the invention is to provide for image enhancement over that produced by conventional imaging systems.

Another aspect of the invention is to provide for increased scan speeds by reducing the number of projections or flux needed for a given image quality.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWINGS

The invention will be more fully understood by reference to the following drawings which are for illustrative purposes only.

DETAILED DESCRIPTION OF THE INVENTION

Referring more specifically to the drawings, for illustrative purposes the present invention is embodied in the methods generally shown in FIG. 1 through FIG. 5 and the associated diagnostic and computational devices used to perform the methods. It will be appreciated that the apparatus may vary as to configuration and as to details of the parts, and that the methods may vary as to the specific steps and sequence, without departing from the basic concepts as disclosed herein. The method steps are merely exemplary of the order these steps may occur. The steps may occur in any order that is desired, such that it still performs the goals of the claimed invention.

The present invention relates to improved computed tomographic imaging systems that mathematically reconstruct cross-sections of an object from its projections. The number of projections and the exposure of a subject to ionizing radiation such as X-rays can be substantially reduced by reducing scan times through imaging with fewer projections, reduced radiation flux and reduced image noise without losing the fine image features in the process.

Figure 1:
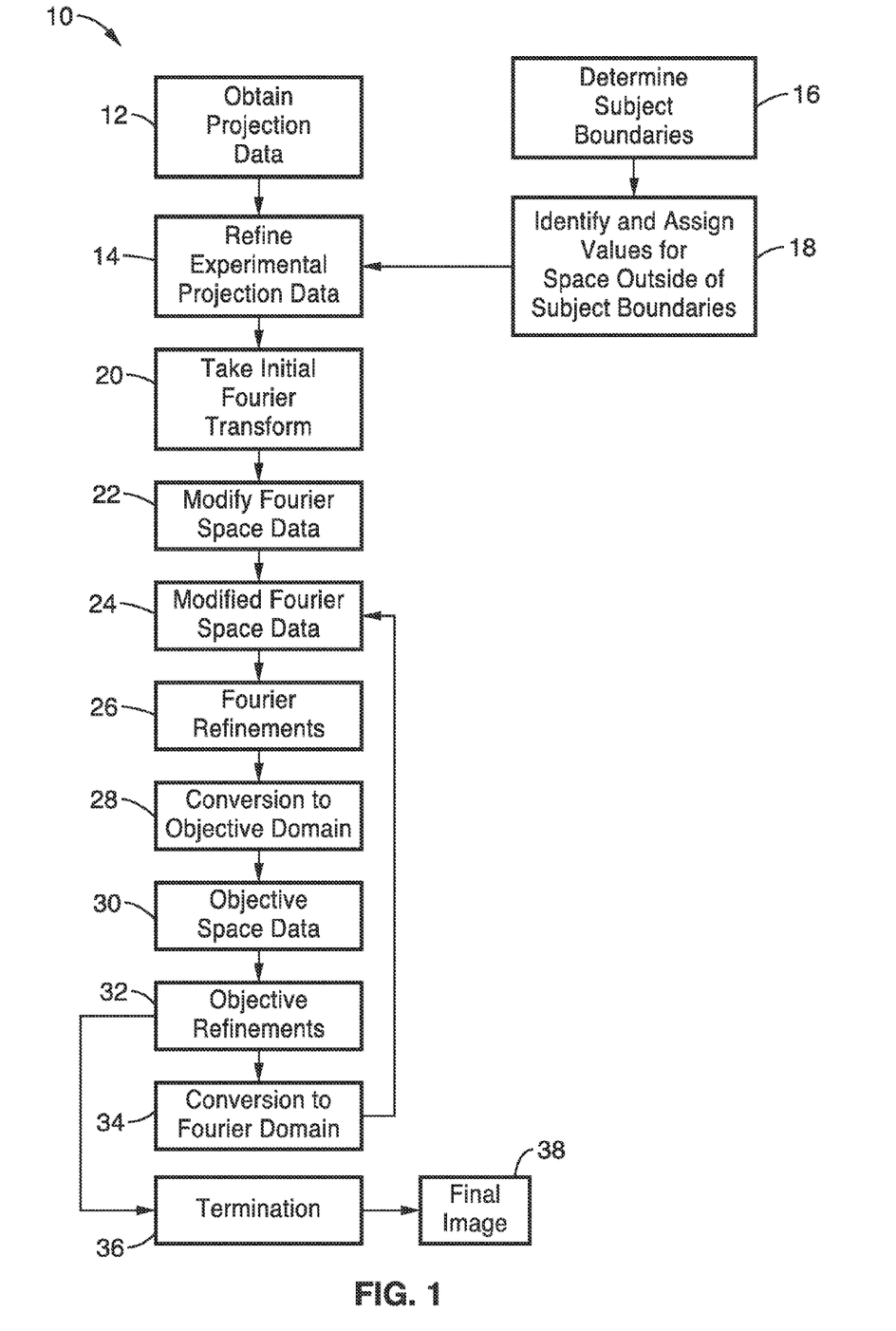
FIG. 1 is a flow diagram for a method for fast implementation of equally sloped tomography for dose reduction and image enhancement according to one embodiment of the invention.
Figure 2:
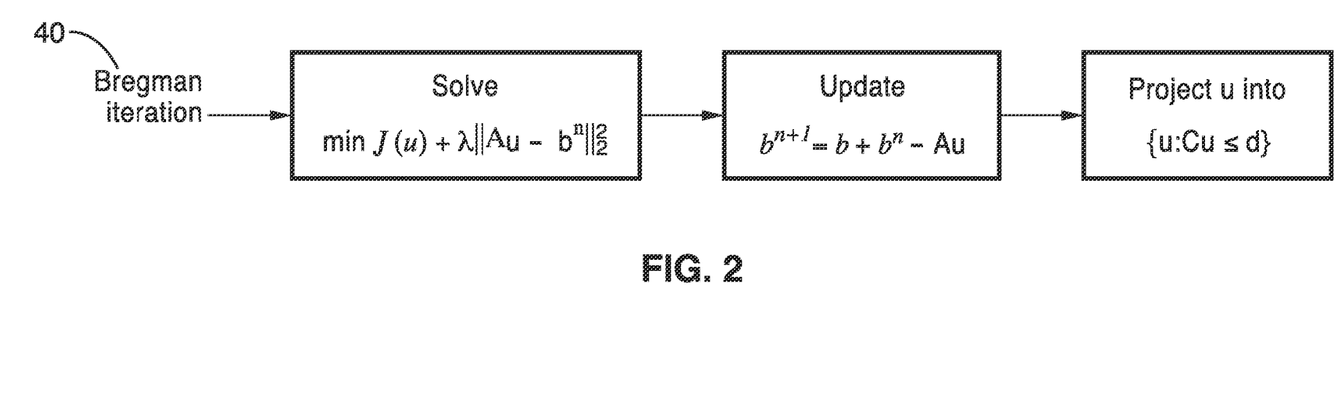
FIG. 2 depicts a Bregman iteration type of sub-transformation algorithm according to one embodiment of the invention.
Figure 3:
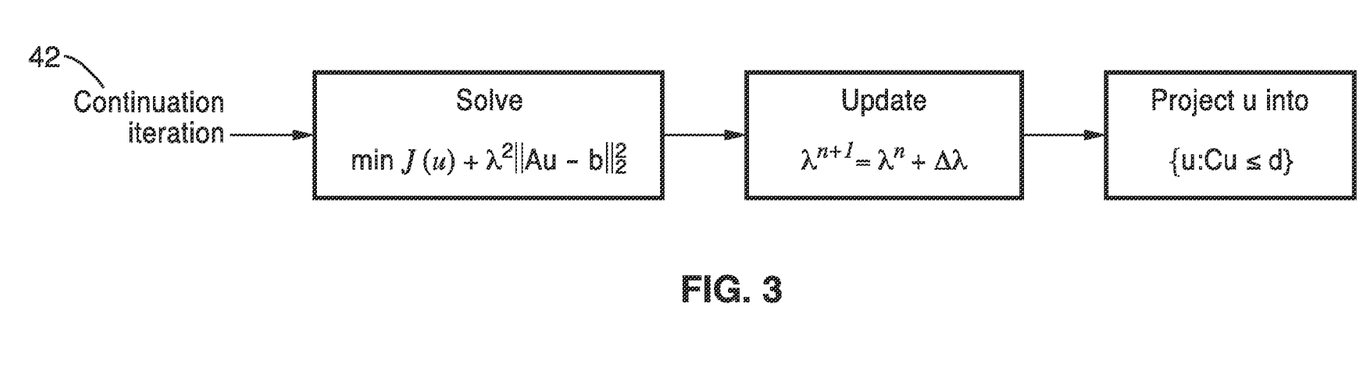
FIG. 3 depicts a Continuation iteration type of sub-transformation algorithm according to one embodiment of the invention.

Turning now to the flow diagram depicted in FIG. 1, one embodiment 10 of the invention is schematically shown. In FIG. 1, projection data from a parallel beam scanner system is acquired at block 12 and may be recorded and processed with a computer or other recording device. For non-parallel beam systems, projection data may be acquired and then reformulated by a parallel-beam equivalent projection data set. Such reformulation at block 12 can be performed by mathematical transformations in an exact or approximate manner from the system geometry to produce an equivalent parallel beam geometry. The reformulation can also be performed by existing "rebinning" algorithms present in the art which specifically change the projection data from the given system to a parallel beam equivalent system in an exact or approximated method. Another related method includes an interpolation of the sinogram along the desired parallel projection angular location to arrive at a parallel beam projection at block 12.

A further method for converting non-parallel cone or fan beam data to the parallel beam format is provided that comprises a) reconstructing the raw cone or fan beam projection data using standard algorithms for fan/cone beams known in the art, b) operation of a 2D Fourier transform (FT) across all slices, c) extracting the Fourier transformed projections at the desired location from the Fourier data with the use of the Fourier Slice Theorem to arrive at the transformed parallel beam projections, and, d) optionally, if an object space projection data set is desired, operating an inverse 1D Fourier transform to arrive at the parallel beam projection data in object space.

The EST projection data obtained at block 12 are preferably acquired at angles corresponding to the lines of the pseudo-polar grid, which consists of concentric squares with a horizontal and a vertical group of lines. The purpose of such an acquisition, in conjunction with the disclosed imaging methods, is to provide a methodology to completely eliminate deleterious interpolations that riddle conventional tomographic reconstruction algorithms. With both groups of lines on the pseudo-polar grid, the lines are aligned such that the slopes of the lines form an arithmetic sequence (i.e. the difference of the slope between two consecutive lines is a constant and the lines are equally-sloped), whereas in the standard polar grid, the angle between two consecutive lines is a constant (i.e. the lines are equally-angled).

The acquired projection data at block 12 may be recorded and stored or processed transiently in a computer apparatus configured for these purposes. Optionally, the initially acquired parallel beam data at block 12 can be refined through the application of a noise reducing mathematical transformation such a denoising, deconvolution, deblurring, scatter correction, uniformity correction, smoothing, image restoration, or a filtering transformation at block 14. Common examples of the mathematical transformations that can be used to refine the initial projection data at block 14 may include: 1) Wiener filtering/deconvolution and it's many different variants; 2) Rudin-Osher-Fatemi (ROF) total variation (TV) algorithms and their variants; 3) Nonlocal means algorithms; 4) Penalized likelihood method; 5) Kalman filtering/deconvolution and its variants; 6) Speckle filtering; 7) Simple filters such as Gaussian filters, Laplacian filters, low pass filters, high pass filters, edge enhancing filters; 8) Anisotropic filters; 9) Deconvolution algorithms based on a known or user defined point spread function; 10) Wavelet denoising; 11) Neighborhood filters and the SUSAN filter; 12) Discrete universal denoiser; and 13) unsupervised information-theoretic, adaptive filtering as well as a variety of other transformations.

In addition, the expected values of the surroundings of the patient or object may be determined and optionally utilized in the image reconstruction process to further reduce computation time, radiation dose and the number of projections as well as increase the image definition to enhance the final image. The typical scanner will attempt to resolve the whole field of view of the scanner including the background surroundings of the subject such as the surrounding air volume, the bed and the object support modules. This process creates the need for a higher number of projections for an adequate reconstruction of the subject and utilizes significant computational resources.

The characteristics of the scanner and the surroundings are identified and categorized and located in three dimensional space in the embodiment shown for some or all possible scan protocols and scanner configurations. This profile information may be stored in data storage for access and use with the other computer tomography programming. Accordingly, at block 16 and block 18 of FIG. 1, a profile of the scanner and subject surroundings is created in this embodiment. The produced profile will preferably account for the type of scanner that is used, the scan parameters and the characteristics of the subject that is being scanned. For example, conventional scanners may have one of several different types of beam sources including photons, electrons, protons, ions, neutrons and sound waves.

In one preferred embodiment, the expected voxel values of the subject's surroundings at Block 16 are determined by performing a set of scans without the subject in the scanner using many different scan parameters and scanner configurations in order to produce a reference data set with the approximate voxel values for each type of scan and scanner configuration. During the reconstruction process, the locations and nature of the patient's surroundings are determined by an initial reconstruction, a set of voxels may be designated as constraints, the expected values of these designated voxels are determined from the reference scans, and these expected values are then utilized to aid in the reconstruction of the subject scan.

Once the parallel beam data or parallel beam equivalent data has been acquired at block 12, optional boundaries and surroundings assigned at block 18 and optional initial preprocessing refinement at block 14 have taken place, a Fourier Transform of each projection is performed at block 20. The type of Fourier transform that is selected will depend on the type of grid in Fourier space that is desired. 'Fourier space' is defined as a space in which at least one Fourier transformation has been applied to a given data set. The Fourier space can also be constructed from other transformations in addition to the Fourier transform. In some situations, the Fourier space used here is similar or equivalent to the phrase 'frequency domain' or 'k-space' in the art.

In one embodiment, the Fourier transform of the projections at a plurality of angles and slices at block 14 is a Fractional Fourier Transform set to match points and lines of a pseudopolar grid for each angle in accordance to the Fourier Slice Theorem. Other computerized implementations of the FT such as the non-uniform Fast Fourier Transform (NUFFT) and the conventional Fast Fourier Transform (FFT), can be utilized at this point in accordance with the Fourier Slice Theorem.

Optionally, the Fourier space data of the projections may then be modified at block 22 of FIG. 1. Other supplemental transforms can also be applied to the projection data at this point as part of the initial Fourier space modifications. For example one supplemental transform includes a Fourier Transform across all slices in the Fourier space to correlate the Fourier space data.

Preconditioning methods at block 22 may also include assigning values to the missing Fourier space data based on the reconstruction of the projection data by any method known in the art. The Fourier data and grid may also be modified at this point by extending the grid and padding the Fourier space data with zeros. Other modifications may include the enforcement of Fourier space conditions such as symmetry conditions on the phase or amplitude of the Fourier data.

One embodiment of the method uses 'oversampling.' When a Fourier slice is sampled at a frequency finer than the Nyquist interval, the corresponding projection in the object domain is surrounded by mathematical zeros. If the Fourier slices that are calculated from the measured projections are oversampled, the 3D object to be reconstructed should be surrounded with zeros. These mathematical zeros do not provide extra information about the 3D object but will help to extract the correlated information among the Fourier slices.

If oversampling was used, the physical image region is preferably surrounded by a known number of pixels with values equal to zero. The pixels in this region, referred to as the support, can be used as an additional constraint. Consequently, the object space can be further modified in the support region by pushing the non-zero pixel values in this region towards zero. This method aids the reconstruction by providing additional constraints through which the object space can be modified.

The Fourier transforms of the refined projections are placed on a grid in Fourier space at block 24. The projections at each angle are preferably mapped to their corresponding lines on the pseudopolar grid in the Fourier space, preferably using the Fractional Fast Fourier Transform (FrFFT).

The placement of transformed projections onto a grid in Fourier space may also be performed with an exact or approximate mathematical transformation, or by interpolating the location and values of a transformed projection on the Fourier space grid. The placement of transformed projections onto a grid in Fourier space may also be performed by the Gridding method. The present invention is not restricted to any specific grid in Fourier space. Other grids that may be used for the Fourier space data include Cartesian type, polar type, 3D polar (i.e., spherical) type, 3D pseudopolar and others.

The parallel beam projections that are transformed into the Fourier domain using Fractional Fourier Transform (FrFT) at block 24 are used to reconstruct an image represented as a constrained optimization problem solved by a series of unconstrained linear problems.

In a preferred embodiment, the method is formulated as a constrained optimization problem that is solvable by a gradient descent algorithm that additionally incorporates a mathematical regularization method called the Non-Local Means Total Variation model generally described at blocks 26 through 38.

After the measured projections are converted to Fourier slices by using the fractional FFT at block 24, constraints and refinements in the Fourier domain may be applied at block 26. Initially there will not be any refinements in the first cycle because these have been performed previously at block 22.

The projections are converted to the objective domain at block 28 to provide object space data at block 30. Physical and mathematical constraints can be applied in the objective domain at block 32. In one embodiment, the calculated slices are replaced with the corresponding measured ones in the Fourier domain, resulting in a compromise between the enforced constraints and the measured data. Examples of other objective-domain constraints include the zero-density region due to oversampling, positivity and Non-Local Means Total Variation.

The constrained and refined object space data derived at block 32 is converted to the Fourier domain at block 34 and the algorithm then iterates back and forth between real and Fourier domains. The transformation between real or objective domain and Fourier domain is preferably implemented by the Pseudo-polar FFT (or some other direct and exact fast Fourier transform algorithm) and the preconditioned conjugate gradient method. By using this exact Fourier-based iterative algorithm as well as physical and mathematical constraints, the optimized method enables convergence to a lowest-possible noise state that is also strictly consistent with the measured data.

The iterative cycle is terminated at block 36 after a predetermined number of cycles or when no further improvements can be made and a final image is produced at block 38.

The general structure of preferred embodiment is to solve a constrained optimization problem in which the constraints are given by both Frequency measurements and the physical constraints such as positivity and surrounding constraints. To illustrate, a 2D image that is to be reconstructed in the object domain is termed "u" and the pseudo-polar Fourier transform of "u" is termed $\mathcal{F}$. The frequency measurements obtained from the tomography data can be expressed as:

$$S_1 \mathcal{F} u = b_1$$

where S denotes the sampling operator in the frequency domain that selecting the acquired measurements. This can be considered to be a frequency constraint.

Similarly, "physical constraints" in general can be expressed as $$S_0 u = b_0$$

where $S_0$ denotes the sampling operator in the object domain such as selecting pixels with known values if oversampling is used. These linear equality constraints together can be formulated to be $$Au = b.$$

There might be other kinds of physical constraints with given data, e.g. the positivity constraint $u \geq 0$ or the known range of the intensity $a_1 \leq u \leq a_2$ given by experimental settings or previous experiments for the same object (here $a_{1,2}$ can be constants or pixel-dependant arrays). If any measurement that contains heavy noise is obtained and can only be treated as a relaxed range of instead of strict frequency value, it can be expressed as an inequality constraint:

$$b_{21} \leq S_2 \mathcal{F} u \leq b_{22}$$

The preceding linear inequality constraints can be formulated together to be $$Cu \leq d.$$

While a direct least square solution to linear equations can normally be obtained, such a solution is not an optimal one due to the presence of noise. Therefore, in order to obtain the best solution, a regularization functional is preferably applied that quantifies the quality of the reconstructed image. Such a solution optimizes the regularization functional and also is consistent with experimental measurements.

The objective function is a regularization functional that controls the quality of the reconstruction image. There are a variety of choices of this objective function that depend on the prior knowledge of the desired reconstruction:

Preferred embodiment 1: 'objective function' given by the total variation of the image.

$$J(u) := \int_\Omega |\nabla u| dx$$

Preferred embodiment 2: 'objective function' given by the square of the L₂ norm of gradient of the image.

$$J(u) := \int_\Omega |\nabla u|^2 dx$$

Preferred embodiment 3: 'objective function' given by the non-local weighted total variation of the image.

$$J(u) := \int |\nabla_w u| dx = \int_\Omega \sqrt{\int_\Omega (u(x)-u(y))^2 w(x,y) dy}\, dx$$

Preferred embodiment 4: 'objective function' given by the square of the L₂ norm of the nonlocal weighted gradient of the image.

$$J(u) := \int |\nabla_w u|^2 dx = \iint_{\Omega \times \Omega} (u(x)-u(y))^2 w(x,y) dy dx$$

In the embodiments above the nonlocal weight $w_u(x,y)$ is a 2D array depend on u and defined as follows:

$$w_u(x,y) = \exp\left(-\frac{1}{h^2}\int_\Omega G_a(z)|u(x+z) - u(y+z)|^2 dz\right)$$

where $G_a(z)$ is a Gaussian kernel with standard deviation a. The parameter of this Gaussian kernel and the scale parameter h can be designated by the user. The nonlocal weight $w_u$ defined above can be either upgraded as a function of the image during the solving procedure or fixed by initial guess of the image.

Given the preferred objective function, the constrained optimization problem $$\min J(u)\ s.t.\ Au=b, Cu \le d.$$

can be solved by a variety of mathematical methods. When the image is small, the problem can be solved by conventional linear programming methods and software. However, when the image contains a large number of pixels, this constrained problem is preferably solved by solving a series of unconstrained problems:

$$\min_u J(u) + \lambda H(u)$$

where H(u) is a quadratic penalty term corresponding to the overall constraints. There are two preferred iterative methods that can be used to solve the constrained problem by the sequence of unconstrained problems: the Bregman iteration 40 illustrated in FIG. 2 and the continuation method 42 illustrated in FIG. 3. The iterative loop is preferably terminated with a maximum number of iterations with both the Bergman iteration regularization 40 and the continuation method 42.

Figure 4:
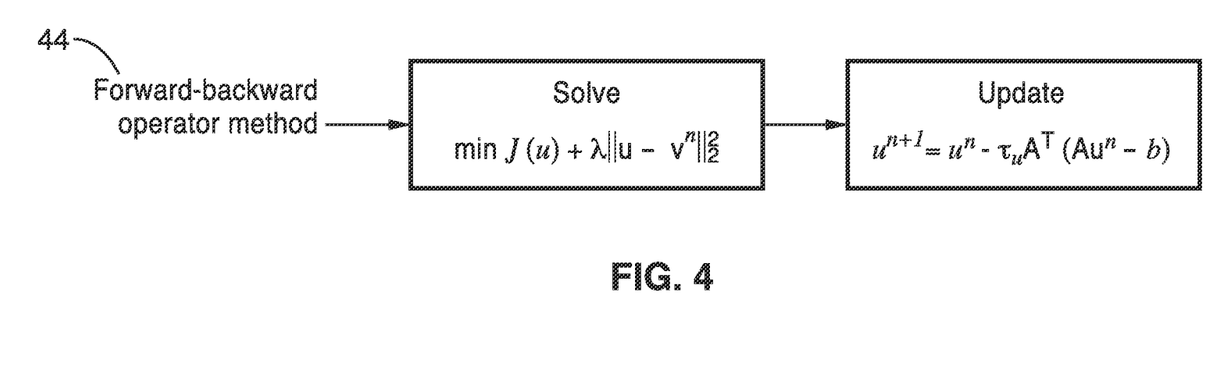
FIG. 4 depicts a forward-backward operator method for solving unconstrained problems diagram according to one embodiment of the invention.

In the preferred embodiment, the unconstrained problem $\min_u J(u) + \lambda \|Au-b\|_2^2$ can be solved by forward-backward operator method 44 as shown in FIG. 4. The operator splitting method 44 was developed to solve the optimization problem when the objective function is the sum of two convex functions.

Figure 5:
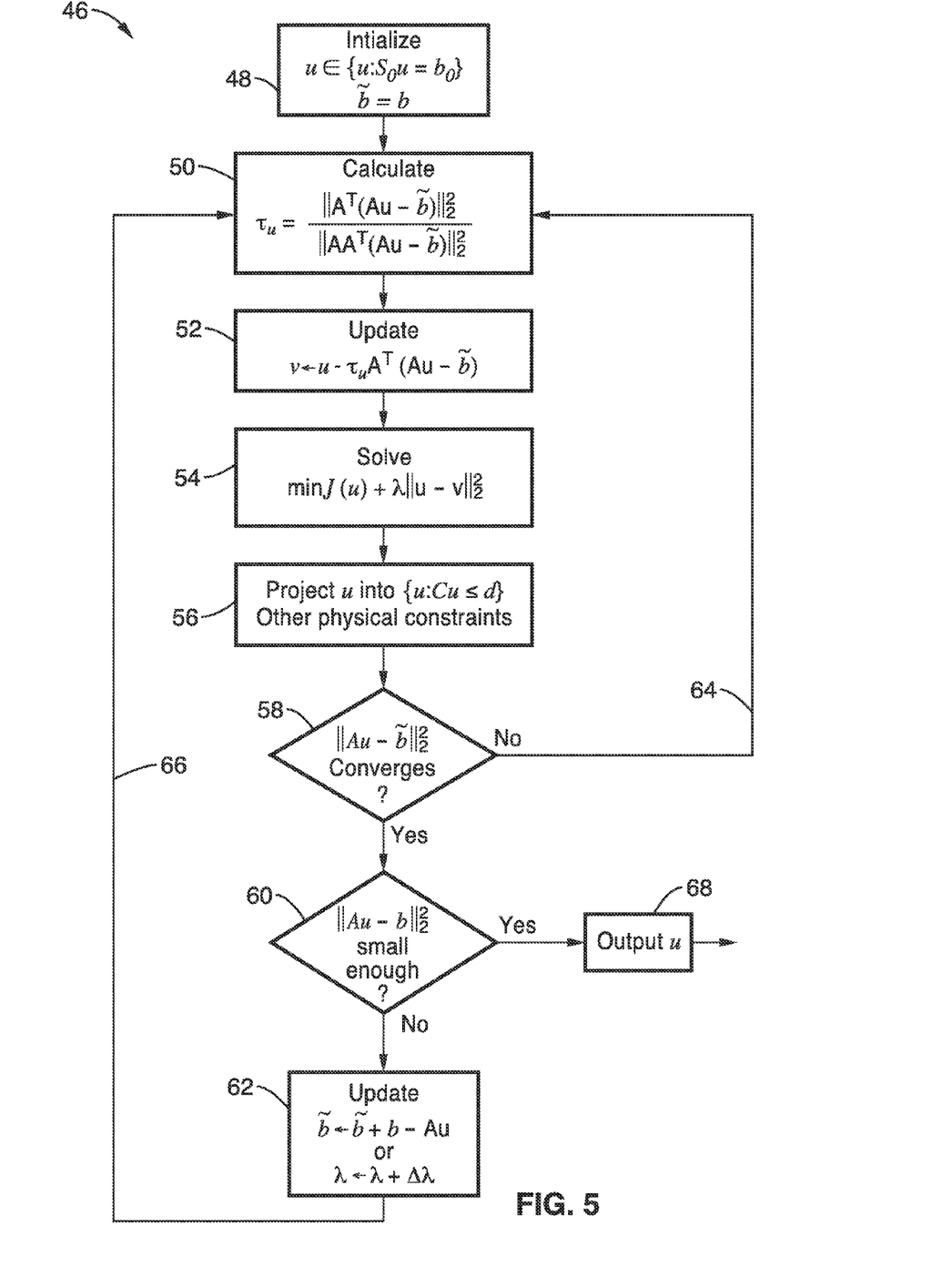
FIG. 5 is a flow diagram for one method for EST tomographic reconstruction according to the invention that transforms a constrained problem to a series of linear problems that are solved by the operator splitting method.

Referring also to FIG. 5, these elements are combined together to provide reconstruction of 2D slices "u" with the imposition of physical constraints (positivity) and frequency constraints. The reconstruction is represented as a constrained problem that is solved iteratively by a sequence of unconstrained problems.

In the embodiment 46 of the method shown in FIG. 5, the projection data is acquired from a scanner and the slices initialized at block 48. Preprocessing of the acquired data and transformation into the Fourier domain may be part of the initialization step at block 48. In addition, the identification and selection of frequency and physical constraints may also be part of the initialization at block 48.

The initialized and pre-processed slice data at block 48 is sent through a series of manipulations and refinements beginning at block 50. The calculated time results at block 50 are updated at block 52 and a minimization problem solved at block 54 that is projected into the object domain with selected restraints at block 56.

It can be seen that the embodiment 46 of the method shown in FIG. 5 has two levels of iterations, an inner loop 64 and an outer loop 66, and each level needs an appropriate stop criterion.

For the inner loop 64, i.e. the forward-backward operator splitting iteration with the sequence defined by blocks 50 through 58, the iteration can be terminated at block 60 when the relative decrease of H(u) is smaller than a certain threshold, or after a fixed number of iterations. For example, the inner loop could be terminated at block 60 with the appearance of a termination condition such as when the residue $\|Au-b^n\|_2^2$ is small enough or the number of iterations reaches the maximum iteration. The length of the time step τ is preferably optimized at block 50 by the line search scheme $$\tau_u = \frac{\|A^T(Au-b)\|_2^2}{\|AA^T(Au-b)\|_2^2}.$$

The first minimization problem in the above embodiment $$\min J(u) + \lambda \|u-v^n\|_2^2$$

can be solved at block 54 with various methods depending on the choice of J(u). When J(u) is given by the total variation of the image, this problem coincides to the ROF model and can be solved at block 54 by the graph cut method efficiently. When J(u) is the square of the L₂ norm of gradient of the image, this coincides to the Wiener model and can be solved by Wiener filter. When J(u) is given by the non-local weighted total variation or the square of the L₂ norm of the nonlocal weighted gradient, this problem can be solved by nonlocal denoising method with the nonlocal weight $w_u(x,y)$ either upgraded after each outer loop during the solving procedure or fixed by initial estimation of the image.

For the outer loop 66, defined by a positive decision at block 58, a negative decision at block 60, and alternative iterative regularizations at block 62, and back to block 50, very few iterations are typically needed. Numerical experiments show that generally 2-3 iterations can provide a good performance. In one embodiment, the parameter of exceeding a threshold of the residual H(u) is used to automatically terminate the iteration. The purpose of the outer loop is to iteratively "squeeze" information from the measurements. Too many outer iterations using the Bregman Iterative Regularization or the Continuation method at block 62 has the potential for introducing high noise into the image, especially when the measurements contain significant noise. Since the details and artifacts are brought back to the image gradually, under certain environments it is possible to let users judge the quality of images after each outer iterative step and manually terminate the outer iteration at a proper time.

When both conditions at decision block 58 and decision block 60 are positively satisfied, the final image is produced at block 68. In one embodiment, a post "legitimation" procedure is applied before finalization of the image by correcting the measured Fourier coefficients of the image in the frequency domain. Since the image has converged to a less noisy state during the previous steps, this final step will not bring back a lot of noise (although the image may be degraded if the data itself is noisy).

The invention may be better understood with reference to the accompanying examples, which are intended for purposes of illustration only and should not be construed as in any sense limiting the scope of the present invention as defined in the claims appended hereto.

Example 1

In order to demonstrate the functionality of the invention and the general principles behind the image refinement methods, comparative reconstructions of a phantom were conducted.

The method of one embodiment of the invention was compared with the conventional filtered back projection (FBP) approach as a function of projections and fluence. The number of projections and the fluence of the illumination particles are two factors that influence the quality of the reconstructed image and the radiation dose in tomography. The number of projections determines how many measurements, i.e. linear constraints on the image, and the fluence of the imaging system determines the magnitude of noise in the measurements. It was shown that the methods of the invention perform far better than FBP, using fewer projections and less fluence, permitting dose reduction without reducing the quality of the reconstructed images.

To quantify the quality of image reconstruction of the methods for complex objects, numerical simulations on slice 82 of the Zubal anthropomorphic head phantom were performed. The values that were assigned to the organs represent x-ray attenuation coefficients corresponding to a TASMIP x-ray spectra calculated for 120 kvp and 2 mm resulting in a mean flux weighted energy of 56.4 key. In the numerical simulations, calculations of the 360, 90, 60, 45 projections were made and Poisson noise was added to the projections with a fluence of $7.0 \times 7.0 \times 10^5$ m$^{-2}$.

Images from the same projection data were reconstructed by FBP, the standard Equally Sloped Tomography iterative method (EST iterative), the EST Bregman iterative method (EST Bregman) and the EST continuation method (EST continuation) and the fine features of the images were compared. To quantify the reconstructions, a Fourier Ring Correlation (FRC) was used to measure the correlation of the reconstructed images to the original phantom as a function of spatial frequency. A FRC value of 1 represents 100% correlation while a value of 0 represents 0% correlation; the spatial frequency defined by the 0.5 value of the FRC curve, representing 50% correlation between reconstructed image and the original phantom, is commonly taken as a numerical value of the resolution.

It was observed that the quality of reconstructed images from 360, 90, 60 and 45 projections using with the EST methods was significantly better than FBP. With the same number of projections, the EST methods outperform FBP in all spatial frequencies, indicating higher resolution and correlation for the EST reconstructions. It was also observed that the differences between the three EST methods are relatively small when the number of projections is large, but becomes large when the number of projections is reduced. Furthermore, when there is a limited number of projections, the EST Bregman reconstruction shows more fine features that the EST iterative reconstruction.

The improvement is mainly due to the outer iterative loop in the EST Bregman and continuation algorithms, which can obtain fine features from noisy data more efficiently. As importantly, by replacing the inverse Fourier transformation with the Peudo-polar Fourier Transform, the computational time in each iteration is reduced by approximately 70%, and the total number of iterations is reduced by approximately 50% due to the more efficient convergence strategy. Therefore, even with the extra outer iterative loop in the new algorithms, the overall computation time is significantly reduced, as shown in Table 1. Although the new algorithms still require more computation power than FBP, they can in principle be implemented in clinical CT scanners by parallel computing and fast FFT based processors such as graphical processing units (GPUs).

It was further observed that the EST Bregman reconstruction from 45 projections is as good as the FBP reconstruction from 360 projections, which corresponds to dose reduction of 87.5%. Dose reduction numerical experiments were also performed by reducing the fluence and comparing the FBP, EST iterative, EST continuation and the EST Bregman reconstructions from 360 and 45 projections with a fluence of $3.5 \times 10^5$ m$^{-2}$, respectively. The EST Bregman reconstruction from 45 projections was still comparable to the FBP reconstruction from 360 projections, which corresponds to dose reduction of 93.5%. The significant dose reduction of the EST method is though to be due to the fact that the method does not interpolate the missing projections from the measurements, but directly searches for the "best" image from the acquired measurements by using advanced iterative algorithms.

Example 2

An embodiment of the method incorporating a Gradient Descent algorithm with mathematical regularization constraints, including the Non-Local Means Total Variation model was used to conduct a series of comparative experiments to quantify the image quality, and explore radiation dose reduction in a CT imager through the reduction of X-ray flux. A standard quality control phantom containing multiple contrast visibility and resolution inserts was imaged using a Siemens Somatom Sensation 64 scanner. The X-ray flux was systematically lowered from 583 mAs to 39 mAs. All scans were performed under axial mode with constant tube current. Comparison reconstructions were produced by Filtered-Back Projection (FBP) with a standard uncropped ramp filter. The resolution, signal-to-noise ratio (SNR) and contrast-to-noise ratio (CNR) were measured and compared as a function of flux.

Pursuant to the methods, the measured projections were transferred to Fourier slices by using the fractional FFT. The algorithm then iterated back and forth between real and Fourier domains. The transformation between real and Fourier domains was implemented by the Pseudo-polar FFT (a direct and exact fast Fourier transform algorithm) and the preconditioned conjugate gradient method. Physical and mathematical constraints were applied in the real domain, while the calculated slices are replaced with the corresponding measured ones in the Fourier domain, resulting in a compromise between the enforced constraints and the measured data. Other real-domain constraints included the zero-density region due to oversampling, positivity and Non-Local Means Total Variation. The reconstruction was monitored by an error metric, defined as the difference between the measured projections and those that were calculated from the reconstructed object, and was automatically terminated when no further improvement could be made. By using this exact Fourier-based iterative algorithm as well as physical and mathematical constraints, the optimized EST technique enables convergence to a lowest-possible noise state that is also strictly consistent with the measured data.

The reconstruction results were also computed by FBP for various phantoms and regions along with the corresponding low-dose gradient descent EST results at a flux of 50 mAs and then compared. Mean value and standard deviation values at various contrast regions were measured to calculate the signal-to-noise ratios (SNRs) and the contrast-to-noise ratios (CNRs). Table No. 2 shows the SNRs and CNRs of the FBP and EST reconstructions with different x-ray flux for the regions defined in the selected images. The quantitative results and the visual comparison indicate that the optimized EST method may enable reduction of CT doses up to 90% through the reduction of flux since radiation dose is linearly proportional to the X-ray flux. Comparable image quality, resolution and contrast as found with the full-dose FBP reconstruction was found with significantly fewer projections and radiation dose with the EST system. Some of the reasons that the EST system allows for significant reduction of the CT dose are because (i) an exact Fourier-based iterative algorithm is used in the reconstruction where both physical and mathematical constraints can be naturally incorporated, (ii) the algorithm is guided towards a lowest-possible noisy state, which is also strictly consistent with the measured data.

Compared to the FBP reconstruction of 500 mAs, the optimized EST reconstruction of 50 mAs was shown to have comparable SNRs and CNRs. The low-contrast regions of the phantom exhibited similar visibility. In addition, no resolution degradation was observed in the low-dose EST reconstruction. Although EST can readily incorporate a priori knowledge, it is noted that such knowledge of the phantom was not utilized in these phantom reconstructions in order to isolate the effect of the algorithm independent of a priori knowledge.

From the foregoing, it can be seen that the invention provides for achieving dose reduction in tomographic imaging systems by reducing the number of projections needed to achieve a reconstructed image of desired image quality. Such reduction in the number of projections will directly reduce the dose applied to the patient for the scan. In one mode, these methods can be used to achieve a reconstructed image of desired image quality using a lower radiation fluence that is emitted or transmitted by a source or multiple sources. Such reduction in the fluence will directly reduce the dose for the particular scan. In another mode, these methods can be used to improve a given image quality parameter (such as resolution, contrast, signal to noise ratio).

Furthermore, these methods allow the scan time to be reduced by reducing the number of projections. Since the acquisition of each projection requires time, such reduction in the number of projections will directly reduce the total scan time for many imaging systems. Still further, these methods allow the scan time to be reduced by reducing the total source flux. Since in general it takes longer for a source to produce a higher flux, such reduction in the total flux will directly reduce the total scan time for many imaging systems.

Embodiments of the present invention are described with reference to flowchart illustrations of methods and systems according to embodiments of the invention. These methods and systems can also be implemented as computer program products. In this regard, each block or step of a flowchart, and combinations of blocks (and/or steps) in a flowchart, can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts support combinations of means for performing the specified functions, combinations of steps for performing the specified functions, and computer program instructions, such as embodied in computer-readable program code logic means, for performing the specified functions. It will also be understood that each block of the flowchart illustrations, and combinations of blocks in the flowchart illustrations, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s).

Accordingly, various embodiments of the present invention include, but are not limited to:

1. A method for processing a tomographic image of an object by obtaining projection data from an imager and processing the projection data with a computer and software, to create an image by pre-processing the projection data to provide a plurality of pre-processed parallel beam projections; transforming pre-processed parallel beam projections into the Fourier domain; converting iteratively the transformed beam projections from Fourier domain to object domain while applying physical and frequency constraints with each iteration until a termination condition is satisfied to produce constrained beam projections; and then generating an image from the constrained beam projections.

2. A method according to embodiment 1, wherein pre-processing comprises a process selected from the group of processes consisting of binning, smoothing, denoising, scatter correction, uniformity corrections and mathematical transformation of the projection data.

3. A method according to embodiment 1, wherein pre-processing comprises changing detected intensities to attenuation coefficients.

4. A method according to embodiment 1, wherein pre-processing comprises applying a rebinning transformation to transform the data into parallel beam format at predetermined angles.

5. A method according to embodiment 4, wherein the predetermined angles correspond to the angles of user determined lines of the 'equally-sloped' pseudopolar grid.

6. A method according to embodiment 4, wherein data from the predetermined angles are used to interpolate to lines of the pseudopolar grid in Fourier space.

7. A method according to embodiment 4, wherein the transformation of parallel beam projections into the Fourier domain is a Fractional Fourier Transform (FrFT).

8. A method according to embodiment 4, wherein the transformation of parallel beam projections is a forward Pseudopolar Fast Fourier Transform.

9. A method according to embodiment 1, further comprising controlling the quality of a reconstructed image with an objective regularization functional selected from the group consisting of a function given by the square of the $L_2$ norm of gradient of an image, a function given by the non-local weighted total variation of an image, and a function given by the square of the $L_2$ norm of the nonlocal weighted gradient of an image.

10. A method for processing a tomographic image of an object, by obtaining projection data from a scanner; and processing the projection data with a computer and software, comprising: pre-processing projection data to provide a plurality of pre-processed parallel beam projections; applying a rebinning transformation to transform the data into parallel beam format at predetermined angles; transforming generated parallel beam projections into the Fourier domain using Fractional Fourier Transform (FrFT); formulating a constrained optimization problem with constraints in Fourier and objective domains and the transformed projections; solving the formulated constrained optimization problem with a gradient descent algorithm; and generating an image from the constrained beam projections.

11. A method as in embodiment 10, wherein the pre-processing comprises a process selected from the group of processes consisting of binning, smoothing, denoising, scatter correction, uniformity corrections, mathematical transformation of the projection data and changing detected intensities to attenuation coefficients.

12. A method as in embodiment 10, wherein the constraints comprise at least one physical constraint and at least one Fourier constraint.

13. A method as in embodiment 12, wherein the Fourier constraint comprises replacement of calculated slices with slices measured in the Fourier domain.

14. A method as in embodiment 12, wherein the physical constraint comprises a constraint selected from the group of constraints consisting of oversampling, positivity, intensity range and non-local means variation constraints.

15. A method as in embodiment 10, wherein the constrained optimization problem is solved with an operator splitting Bregman regularization algorithm.

16. A method as in embodiment 10, wherein the constrained optimization problem is solved with an operator splitting continuation regularization algorithm.

17. A method as in embodiment 1, further comprising: controlling the quality of a reconstructed image with an objective regularization functional selected from the group consisting of a function given by the square of the $L_2$ norm of gradient of the image, a function given by the non-local weighted total variation of the image, and a function given by the square of the $L_2$ norm of the nonlocal weighted gradient of the image.

18. A computer program product comprising a computer-readable storage medium having computer-readable program code portions stored therein and providing for associative relevancy knowledge profiling, the computer program product comprising: a first program code configured for obtaining projection data from a scanner or a scanner electronic storage file; a second program code configured for pre-processing projection data to provide a plurality of pre-processed parallel beam projections; a third program code configured for transforming pre-processed parallel beam projections into the Fourier domain; a fourth program code configured for converting iteratively the transformed beam projections from Fourier domain to object domain while applying physical and frequency constraints with each iteration until a termination condition is satisfied to produce constrained beam projections; and a fifth program code configured for generating an image from the constrained beam projections.

19. A computer program product according to embodiment 18, wherein the third program code comprises a Fractional Fourier Transform (FrFT) or a forward Pseudo-polar Fast Fourier transform (PPFFT).

20. A computer program product according to embodiment 18, wherein the fourth program code comprises a gradient descent algorithm incorporating a Bregman iterative regularization.

21. A system for producing a tomographic image of an object, comprising a scanner capable of producing a plurality of 2D projections of an object; and a computer with software executable on said computer configured to receive the plurality of 2D projections and process said projections, the processing comprising pre-processing projection data to provide a plurality of pre-processed parallel beam projections; transforming pre-processed parallel beam projections into the Fourier domain; converting iteratively the transformed beam projections from Fourier domain to object domain while applying physical and frequency constraints with each iteration until a termination condition is satisfied to produce constrained beam projections; and generating an image from constrained beam projections.

22. A system according to embodiment 21, further comprising a display coupled to said computer wherein said projections and said generated image are displayed.

23. A system according to embodiment 21, where the processing of 2D projections further comprises applying a rebinning transformation to transform the data into parallel beam format at predetermined angles.

24. A system according to embodiment 21, wherein the pre-processing comprises a process selected from the group of processes consisting of binning, smoothing, denoising, scatter correction, uniformity corrections, mathematical transformation of the projection data and changing detected intensities to attenuation coefficients.

25. A system according to embodiment 21, wherein the constraints comprise at least one physical constraint and at least one Fourier constraint.

26. A system according to embodiment 25, wherein said Fourier constraint comprises replacement of calculated slices with slices measured in the Fourier domain.

27. A system according to embodiment 25, wherein the physical constraint comprises a constraint selected from the group of constraints consisting of oversampling, positivity, intensity range and non-local means variation.

28. A system according to embodiment 21, wherein the constrained optimization problem is solved with an operator splitting Bregman regularization algorithm.

29. A system according to embodiment 21, wherein the constrained optimization problem is solved with an operator splitting continuation regularization algorithm.

30. A system according to embodiment 21, further comprising controlling the quality of a reconstructed image with an objective regularization functional selected from the group consisting of a function given by the square of the $L_2$ norm of gradient of an image, a function given by the non-local weighted total variation of an image, and a function given by the square of the $L_2$ norm of the nonlocal weighted gradient of an image.

Although the description herein contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art. In the appended claims, reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present disclosure. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

| | Signal-Noise-Ratio (Arb. Units) | | | | Contrast-Noise-Ratio (Arb. Units) | | | |
|---|---|---|---|---|---|---|---|---|
| | Region I | Region II | Region III | Region IV | Region I | Region II | Region III | Region IV |
| FBP 500 mAs | 1.06 | 51.98 | 39.02 | 39.11 | 27.96 | 20.90 | 2.20 | 3.83 |
| FBP 50 mAs | 0.49 | 24.79 | 26.55 | 26.74 | 12.71 | 9.78 | 0.86 | 1.40 |
| EST 50 mAs | 1.44 | 53.25 | 49.60 | 45.80 | 30.52 | 22.51 | 2.90 | 3.84 |

TABLE 2

| | Computation Time Comparison | | Fluence 7.0 × $10^5$ m$^{-2}$ | |
|---|---|---|---|---|
| | 360 projections | 90 projections | 60 projections | 45 projections |
| FBP method | 5.27 | 1.46 | 0.95 | 0.77 |
| EST iterative method | 80.06 | 176.78 | 214.03 | 283.14 |
| EST Continuation method | 45.10 | 80.06 | 92.68 | 126.15 |
| EST Bregman method | 39.54 | 50.58 | 77.67 | 95.86 |

Times in seconds

What is claimed is:

1. A method for processing a tomographic image of an object, comprising:
    (a) obtaining projection data from an imager; and
    (b) processing said projection data with a computer and software, comprising:
        pre-processing projection data to provide a plurality of pre-processed parallel beam projections;
        transforming pre-processed parallel beam projections into the Fourier domain using Fractional Fourier Transform (FrFT);
        converting iteratively said transformed beam projections from Fourier domain to object domain with an inverse and forward Pseudo-polar Fast Fourier Transform while applying physical and frequency constraints with each iteration until a termination condition is satisfied to produce constrained beam projections; and
        generating an image from constrained beam projections.

2. A method as recited in claim 1, wherein pre-processing comprises a process selected from the group of processes consisting of binning, smoothing, denoising, scatter correction, uniformity corrections and mathematical transformation of the projection data.

3. A method as recited in claim 1, wherein pre-processing comprises changing detected intensities to attenuation coefficients.

4. A method as recited in claim 1, wherein pre-processing comprises
    applying a rebinning transformation to transform the projection data into parallel beam format at predetermined angles.

5. A method as recited in claim 4, wherein the predetermined angles correspond to the angles of user determined lines of an 'equally-sloped' pseudopolar grid.

6. A method as recited in claim 4, wherein data from the predetermined angles are used to interpolate to lines of a pseudopolar grid in Fourier space.

7. A method as recited in claim 1, further comprising controlling the quality of a reconstructed image with an objective regularization functional selected from the group consisting of a function given by the square of the $L_2$ norm of gradient of the image, a function given by the non-local weighted total variation of the image, and a function given by the square of the $L_2$ norm of the nonlocal weighted gradient of the image.

8. A method for processing a tomographic image of an object, comprising:
    (a) obtaining projection data from a scanner; and
    (b) processing said projection data with a computer and software, comprising:
        pre-processing projection data to provide a plurality of pre-processed parallel beam projections;
        applying a rebinning transformation to transform the data into parallel beam format at predetermined angles;
        transforming generated parallel beam projections into the Fourier domain using Fractional Fourier Transform (FrFT);
        formulating a constrained optimization problem with constraints in Fourier and objective domains and said transformed projections;
        solving the formulated constrained optimization problem with a gradient descent algorithm; and
        generating an image from constrained beam projections.

9. A method as recited in claim 8, wherein said pre-processing comprises a process selected from the group of processes consisting of binning, smoothing, denoising, scatter correction, uniformity corrections, mathematical transformation of the projection data and changing detected intensities to attenuation coefficients.

10. A method as recited in claim 8, wherein said constraints comprise at least one physical constraint and at least one Fourier constraint.

11. A method as recited in claim 10, wherein said Fourier constraint comprises replacement of calculated slices with slices measured in the Fourier domain.

12. A method as recited in claim 10, wherein said physical constraint comprises a constraint selected from the group of constraints consisting of oversampling, positivity, intensity range and non-local means variation.

13. A method as recited in claim 8, wherein said constrained optimization problem is solved with an operator splitting Bregman regularization algorithm.

14. A method as recited in claim 8, wherein said constrained optimization problem is solved with an operator splitting continuation regularization algorithm.

15. A method as recited in claim 8, further comprising controlling the quality of a reconstructed image with an objective regularization functional selected from the group consisting of a function given by the square of the $L_2$ norm of gradient of an image, a function given by the non-local weighted total variation of an image, and a function given by the square of the $L_2$ norm of the nonlocal weighted gradient of an image.

16. A non-transitory computer-readable storage medium having an executable program stored thereon, wherein the program instructs a computer to perform steps comprising:

obtaining projection data from a scanner or a scanner electronic storage file;

pre-processing projection data to provide a plurality of pre-processed parallel beam projections;

transforming pre-processed parallel beam projections into the Fourier domain;

converting iteratively said transformed beam projections from Fourier domain to object domain while applying physical and frequency constraints with each iteration with a Pseudo-polar Fast Fourier transform until a termination condition is satisfied to produce constrained beam projections; and generating an image from said constrained beam projections.

17. A computer program product as recited in claim 16, wherein said transforming of pre-processed parallel beam projections into the Fourier domain comprises a Fractional Fourier Transform (FrFT) or a forward Pseudo-polar Fast Fourier transform (PPFFT).

18. A computer program product as recited in claim 16, wherein said conversion of transformed beam projections comprises a gradient descent algorithm incorporating a Bregman iterative regularization.

* * * * *